(12) United States Patent
Su et al.

(10) Patent No.: US 9,907,117 B2
(45) Date of Patent: Feb. 27, 2018

(54) HEATING DEVICE AND BIOCHEMICAL REACTOR HAVING THE SAME

(71) Applicant: GENEREACH BIOTECHNOLOGY CORP., Taichung (TW)

(72) Inventors: Chen Su, Taichung (TW); Hsiao-Fen Chang, Taichung (TW); Pei-Yu Li, Taichung (TW); Yun-Lung Tsai, Taichung (TW); Ching-Ko Lin, Taichung (TW); Wen-Hao Cheng, Taichung (TW); Pin-Hsing Chou, Taichung (TW)

(73) Assignee: Genereach Biotechnology Corp., Taichung (TW)

( * ) Notice: Subject to any disclaimer, the term of this patent is extended or adjusted under 35 U.S.C. 154(b) by 435 days.

(21) Appl. No.: 14/732,049

(22) Filed: Jun. 5, 2015

(65) Prior Publication Data
US 2016/0242237 A1   Aug. 18, 2016

(30) Foreign Application Priority Data
Feb. 13, 2015  (TW) .............................. 104105135 A

(51) Int. Cl.
| B01L 7/00 | (2006.01) |
| H05B 3/42 | (2006.01) |
| C12M 1/38 | (2006.01) |
| H05B 1/02 | (2006.01) |
| H05B 3/06 | (2006.01) |
| H05B 3/22 | (2006.01) |

(52) U.S. Cl.
CPC .............. *H05B 1/0247* (2013.01); *B01L 7/52* (2013.01); *H05B 3/06* (2013.01); *H05B 3/22* (2013.01); *H05B 3/42* (2013.01); *C12M 1/38* (2013.01); *H05B 2203/016* (2013.01)

(58) Field of Classification Search
None
See application file for complete search history.

(56) References Cited

U.S. PATENT DOCUMENTS

| 9,731,296 | B2 * | 8/2017 | Su .............................. B01L 7/52 |
| 2003/0157563 | A1 * | 8/2003 | Danssaert ................. B01L 7/52 |
| | | | 435/7.1 |
| 2010/0210010 | A1 * | 8/2010 | Lee ........................ B01L 3/5029 |
| | | | 435/288.3 |
| 2013/0109022 | A1 * | 5/2013 | Hwang ..................... B01L 7/52 |
| | | | 435/6.12 |

(Continued)

Primary Examiner — Joseph M Pelham
(74) Attorney, Agent, or Firm — Muncy, Geissler, Olds & Lowe, P.C.

(57) ABSTRACT

The present disclosure relates to a heating device and a biochemical reactor having the heating device. The heating device includes an upper plate, a lower plate, a middle plate, and an electric heating element. The upper plate has an upper heating hole, an upper receiving hole, and an upper conductive layer. The lower plate has a lower heating hole, a lower receiving hole, and a first lower conductive layer. The middle plate is disposed between the upper and lower plates and has a middle heating hole and a middle receiving hole. The upper, middle and lower receiving holes are connected together to form a receiving through hole. The electric heating element is disposed in the receiving through hole and has two terminals connected to the upper conductive layer and the lower conductive layer, respectively.

9 Claims, 9 Drawing Sheets

(56) References Cited

U.S. PATENT DOCUMENTS

| | | | |
|---|---|---|---|
| 2013/0210081 A1* | 8/2013 | Koeda | B01L 7/525 435/91.2 |
| 2013/0260421 A1* | 10/2013 | Yamaguchi | B01L 7/52 435/91.2 |
| 2014/0263279 A1* | 9/2014 | Vandersleen | B01L 7/00 219/477 |
| 2015/0247186 A1* | 9/2015 | Uehara | C12Q 1/6844 506/26 |
| 2016/0175843 A1* | 6/2016 | Su | B01L 7/52 435/303.1 |
| 2016/0242237 A1* | 8/2016 | Su | H05B 1/0247 |
| 2017/0239654 A1* | 8/2017 | Hwang | B01L 3/50851 |

* cited by examiner

HEATING DEVICE AND BIOCHEMICAL REACTOR HAVING THE SAME

BACKGROUND OF THE INVENTION

1. Field of the Invention

The present disclosure relates generally to a temperature control device and more particularly, to a heating device and a biochemical reactor having the heating device.

2. Description of the Related Art

Many biochemical reactors are equipped with heating devices such that biochemical reactions can be carried out in vessels at a particular temperature. A conventional heating device is mainly composed of a substrate, two conductive layers, and a heating element. The substrate includes at least one through hole for insertion of a vessel and at least one receiving hole located adjacent to the through hole for accommodating the heating element. The two conductive layers are formed on a part of the substrate and disconnected to each other. Upper and lower terminals of the heating element are respectively connected electrically to the two conductive layers by respective tin soldering. In use, the heating element can convert the electrical energy into heat energy to heat the vessel.

Because the tin soldering connecting the heating element and the two conductive layers may crack easily due to the stress caused by repeated expansions and contractions, the lifetime of the heating device may be shortened. In addition, during the welding process, a part of molten tin soldering may penetrate into a space between the heating element and a wall of the receiving hole by capillary action or force of gravity, or may be sucked into the space by vacuum suction due to the grounds that a vacuum suction force may be generated inside the space, which becomes a closed space when the welding at an terminal of the heating element is completed and the tin soldering at the other terminal of the heating element stays at a partially molten stage, when the substrate cools down to cause volume reduction of the closed space due to temperature decrease of the air inside the closed space. In this case, the tin soldering at one end of the heating element and the tin soldering at the other end of the heating element are connected to each other in the space. A short-circuit may occur therebetween, thereby lowering the production yield.

SUMMARY OF THE INVENTION

In view of the above-mentioned drawbacks of known heating device, it is an objective of the present disclosure to provide a heating device, which has improved prolonged lifetime and could be produced with improved production yields compared to the known heating device. It is another objective of the present disclosure to provide a biochemical reactor, which has improved prolonged lifetime and could be produced with improved production yields compared to the known biochemical reactor.

To attain the above objectives, the present disclosure provides a heating device which comprises an upper plate, a lower plate, a middle plate, and an electric heating element. The upper plate includes an upper heating hole, at least one upper receiving hole located adjacent to the upper heating hole, and an upper conductive layer. The upper conductive layer has an upper region formed on an upper surface of the upper plate and surrounding the upper receiving hole, and a receiving tube region formed on a wall of the upper receiving hole and connected to the upper region of the upper conductive layer. The lower plate includes a lower heating hole, at least one lower receiving hole located adjacent to the lower heating hole, and a first lower conductive layer. The first lower conductive layer has a lower region covering a lower surface of the lower plate and surrounding the lower receiving hole, and a receiving tube region formed on a wall of the lower receiving hole and connected to the lower region of the first lower conductive layer. The middle plate is disposed between the upper plate and the lower plate and includes a middle heating hole and at least one middle receiving hole located adjacent to the middle heating hole. The upper heating hole, the middle heating hole and the lower heating hole are connected together to form a heating through hole. The upper receiving hole, the middle receiving hole and the lower receiving hole are connected together to form a receiving through hole. The electric heating element is disposed in the receiving through hole and has two terminals, one of which is connected electrically to the upper conductive layer and the other one of which is connected electrically to the first lower conductive layer.

The present disclosure further provides a biochemical reactor comprising the heating device of the present disclosure. The biochemical reactor is adapted for the insertion of a vessel and includes a first body having a first through hole, a second body located under the first body and having a second through hole, and the heating device disposed between the first body and the second body. The heating through hole is connected to the first through hole and the second through hole to form a vessel receiving groove for the insertion of the vessel.

The heating device and the biochemical reactor having the heating device are capable of maintaining the temperature of a part of the vessel at a steady temperature. range, a biochemical reaction can be carried out in the vessel, the heating device and the biochemical reactor further have improved production yield and prolonged lifetime.

DETAILED DESCRIPTION OF EMBODIMENTS

Figure 1:
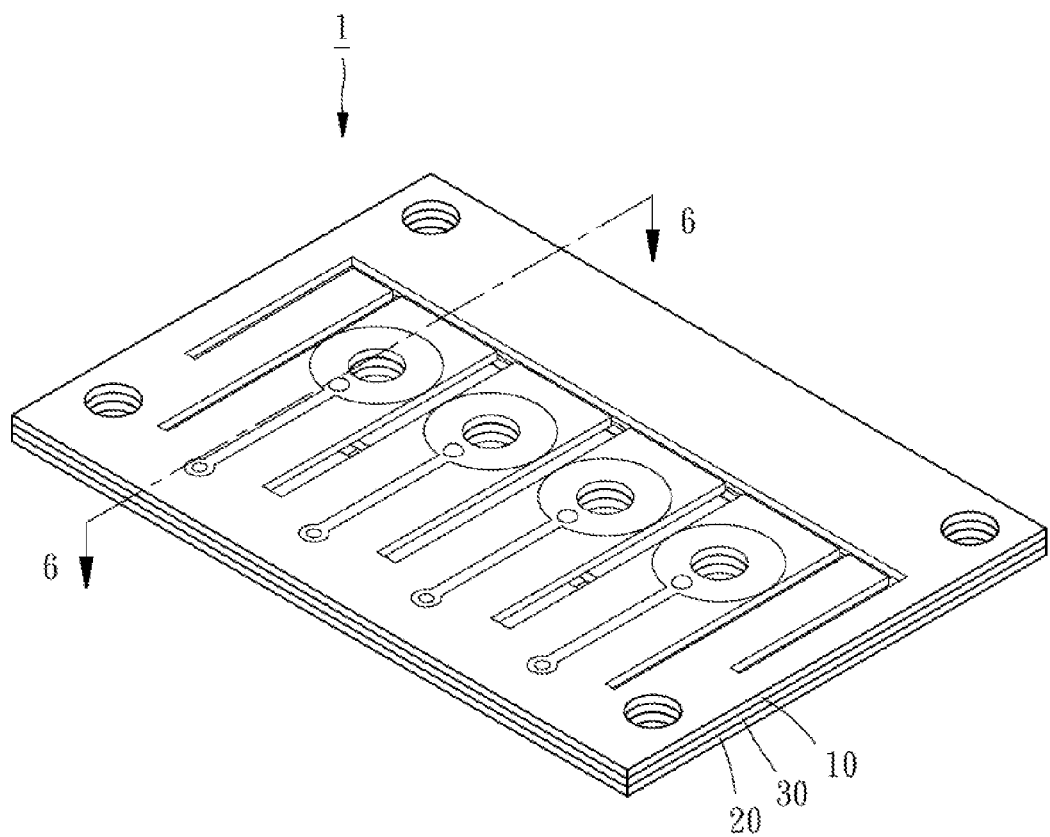
FIG. 1 is a perspective view of a heating device of a first preferred embodiment of the present disclosure.

The structure and the effect of the present disclosure will be understood fully from the detailed description given herein below and the accompanying drawings showing the preferred embodiments of the present disclosure which are given by way of illustration only, and thus are not limitative of the present disclosure. FIG. 1 to FIG. 6 are views of a heating device 1 provided, according to a first preferred embodiment of the present disclosure. The heating device 1 comprises an upper plate 10, a lower plate 20, a middle plate 30, and four electric heating elements 40.

Figure 2:
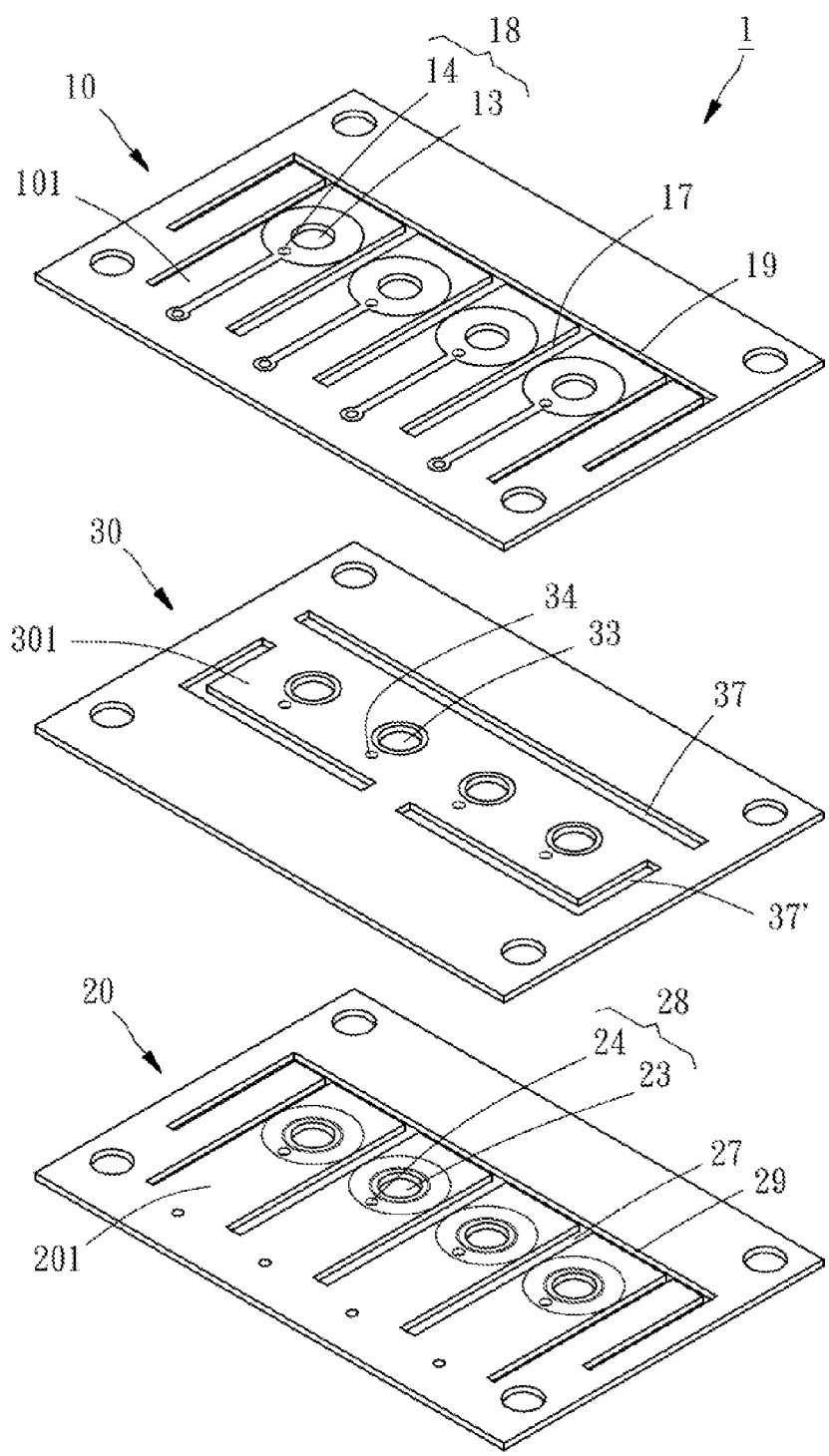
FIG. 2 is an exploded view of the heating device of the first preferred embodiment of the present disclosure.
Figure 3:
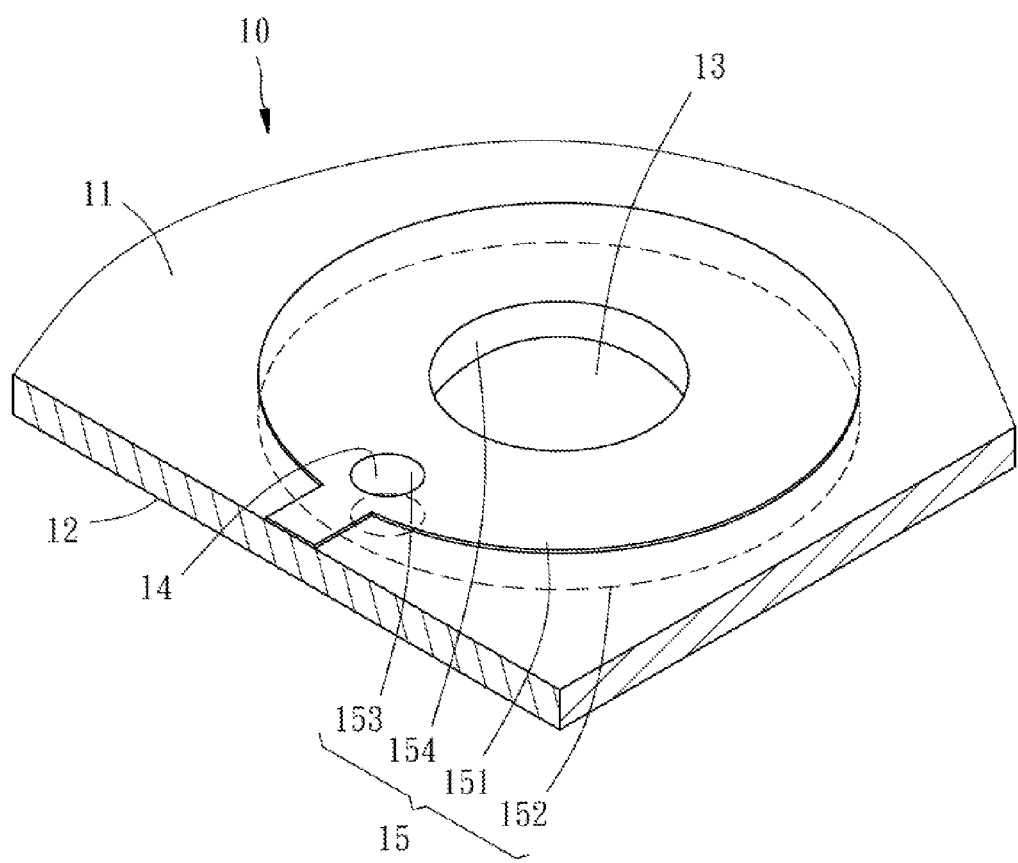
FIG. 3 is a perspective view of a part of an upper plate of the first preferred embodiment of the present disclosure.
Figure 6:
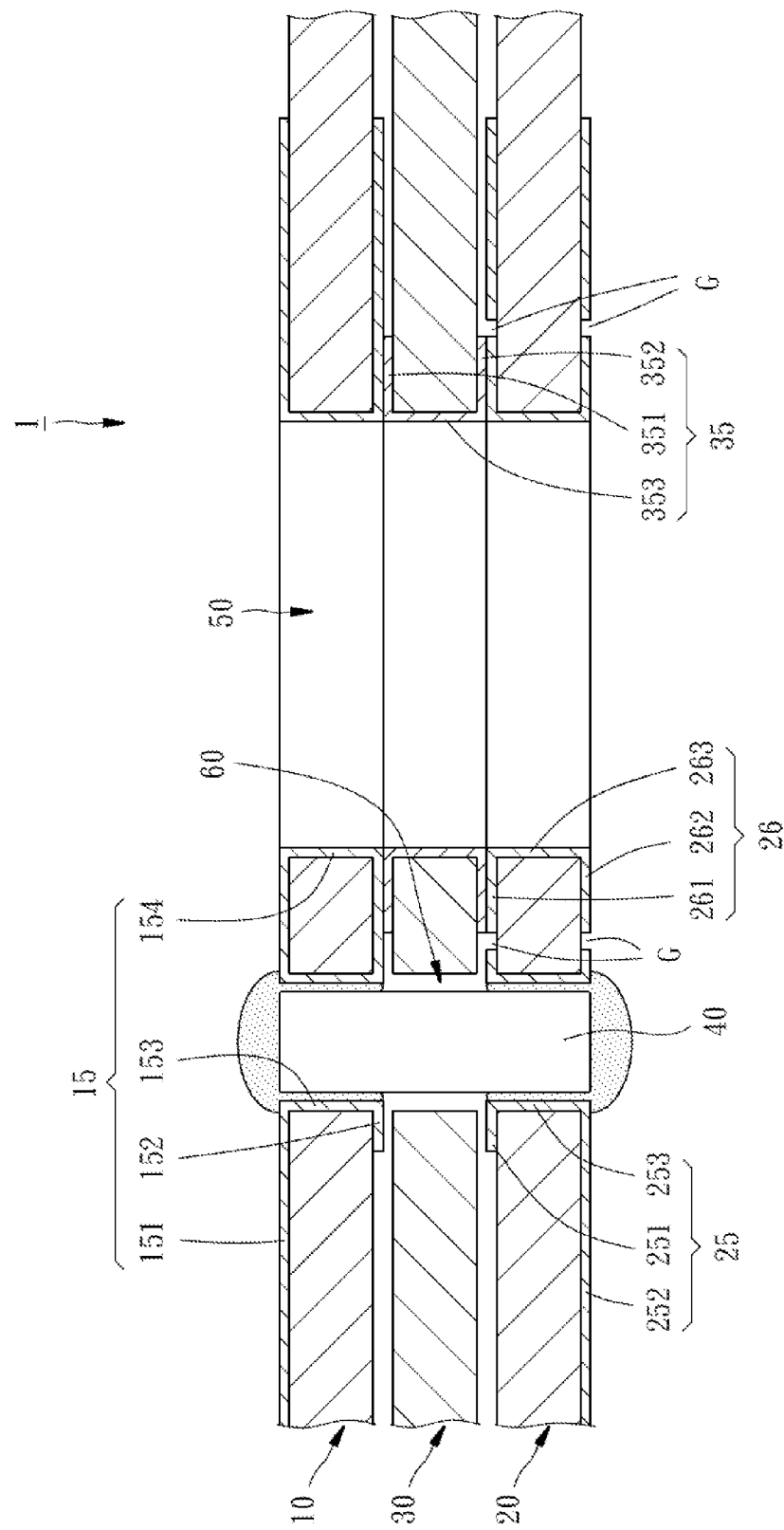
FIG. 6 is a cross-sectional view taken along line 6-6 of FIG. 1.

Referring to FIGS. 2, 3 and 6, the upper plate 10 may be made of an insulated material with acceptable thermal conductivity, such as glass fiber-reinforced resin. The upper plate 10 includes an upper surface 11, a lower surface 12, four upper heating holes 13, four upper receiving holes 14 each located adjacent to one of the four upper heating holes 13, four upper conductive layers 15, an upper longitudinal through groove 19, five upper elongated through grooves 17 extending substantially perpendicular from the upper longitudinal through groove 19 and substantially parallel to each other, and four upper partitions 101 are respectively defined by two upper elongated through grooves 17. Each upper heating hole 13 and the upper receiving hole 14 located adjacent thereto form a hole group 18 and in this embodiment, as shown in FIG. 2, the upper plate 10 has four hole groups 18 each located at one of the four upper partitions 101, which means the five upper elongated through grooves 17 respectively located at the two sides of each hole group 18 to separate the four hole groups 18, in other words, the three sides of each hole group 18 are surrounding by two upper elongated through grooves 17 and the upper longitudinal through groove 19. The upper conductive layer 15 may be made of a material having good electrical conductivity and thermal conductivity properties, such as copper or the like. The upper conductive layer 15 has an upper region 151 formed on the upper surface 11 and surrounding the upper receiving hole 14 and the upper heating hole 13, a lower region 152 formed on the lower strike 12 and surrounding the upper receiving hole 14 and the upper heating hole 13, a receiving tube region 153 formed on a wall of the upper receiving hole 14 and connected to the upper region 151 and the lower region 152, and a heating tube region 154 formed on a wall of the upper heating hole 13 and connected to the upper region 151 and the lower region 152. The upper region 151 and the lower region 152 are respectively shaped as, but not limited to, a ring. In alternate embodiments, the number of the upper receiving hole 14 located adjacent to each upper heating hole 13 is not particularly limited. That is, one or more upper receiving holes 14 may be formed adjacent to each upper heating hole 13.

Figure 5:
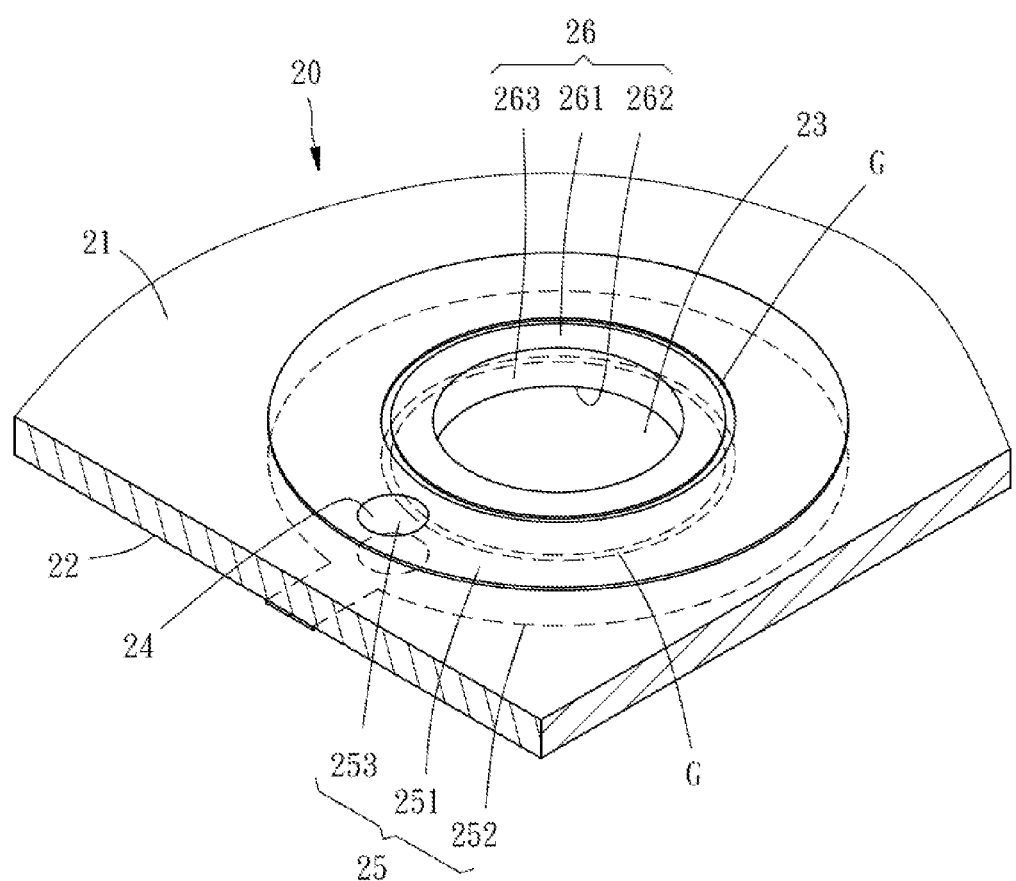
FIG. 5 is a perspective view of a part of a lower plate of the first preferred embodiment of the present disclosure.

Referring to FIGS. 2, 5 and 6, the lower plate 20 may be made of an insulated material with acceptable thermal conductivity, such as glass fiber-reinforced resin. In addition, the lower plate 20 includes an upper surface 21, a lower surface 22, four lower heating holes 23, four lower receiving holes 24 each located adjacent to one of the four lower heating holes 23, four first lower conductive layers 25, four second lower conductive layers 26, a lower longitudinal through groove 29, five lower elongated through grooves 27 extending substantially perpendicular from the lower longitudinal through groove 29 and substantially parallel to each other, and four lower partitions 201 are respectively defined by two lower elongated through grooves 27. Each lower heating hole 23 and the lower receiving hole 24 located adjacent thereto form a hole group 28 and in this embodiment, the lower plate 20 has four hole groups 28 each located at one of the four lower partitions 201, which means the five lower elongated through grooves 27 respectively located at the two sides of each hole group 28 to separate the four hole groups 28, in other words, the three sides of each hole group 28 are surrounding by two lower elongated through grooves 27 and the lower longitudinal through groove 29. The first lower conductive layer 25 may be made of a material having good electrical conductivity and thermal conductivity properties, such as copper or the like. The first lower conductive layer 25 has an upper region 251 formed on the upper surface 21 and surrounding the lower receiving hole 24, a lower region 252 formed on the lower surface 22 and surrounding the lower receiving hole 24, and a receiving tube region 253 formed on a wall of the lower receiving hole 24 and connected to the upper region 251 and the lower region 252. The second lower conductive layer 26 may be made of a material having good electrical conductivity and thermal conductivity properties, such as copper or the like. The second lower conductive layer 26 has an upper region 261 formed on the upper surface 21 and surrounding the lower heating hole 23, a lower region 262 formed on the lower surface 22 and surrounding the lower heating hole 23, and a heating tube region 263 formed on a wall of the lower heating hole 23 and connected to the upper region 261 and the lower region 262. The lower region 252 of the first lower conductive layer 25 further surrounds the lower region 262 of the second lower conductive layer 26 and is spaced from the lower region 262 at a predetermined distance, such that a space G is formed between the lower regions 252, 262. The upper region 251 of the first lower conductive layer 25 further surrounds the upper region 261 of the second lower conductive layer 26 and is spaced from the upper region 261 at a predetermined distance, such that a space G is formed between the upper regions 251, 261. Specifically speaking, the first lower conductive layer 25 is not connected electrically to the second lower conductive layer 26. The upper regions 251, 261 and the lower regions 252, 262 are respectively shaped as, but not limited to, a ring. In alternate embodiment, the number of the lower receiving hole 24 located adjacent to each lower heating hole 23 is not particularly limited. That is, one or more lower receiving holes 24 may be formed adjacent to each lower heating hole 23.

Figure 4:
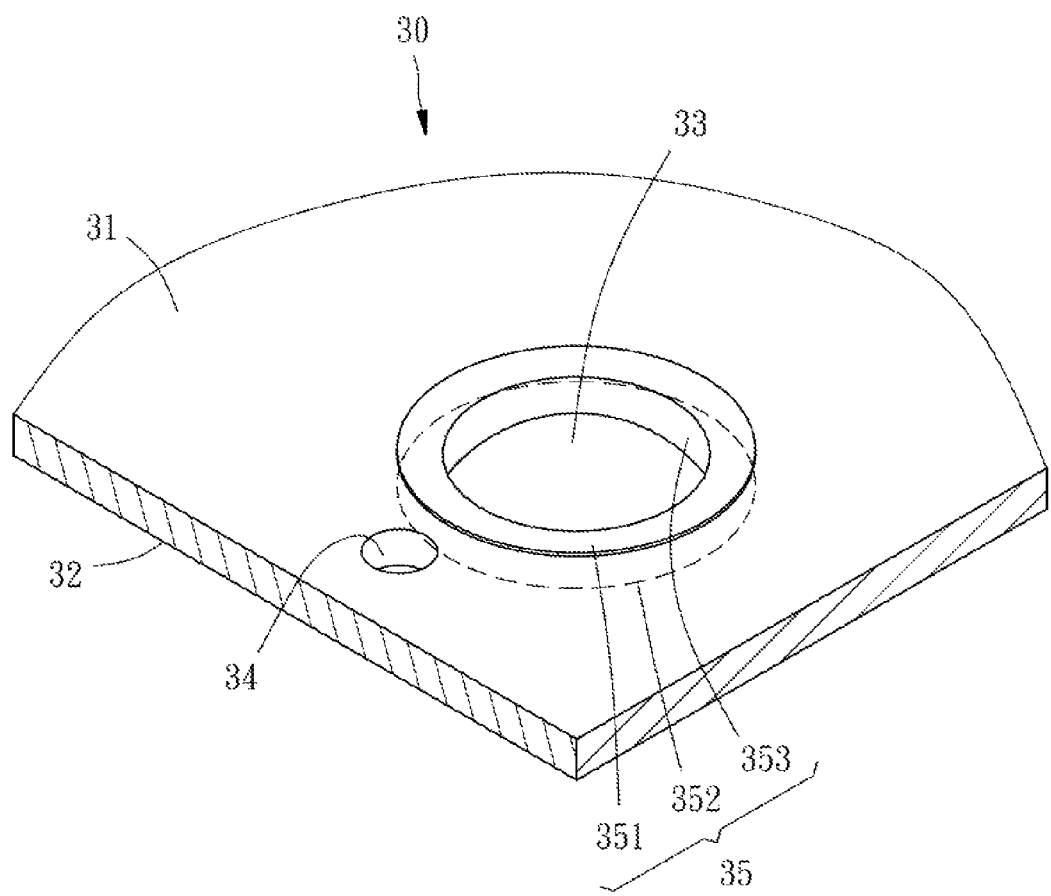
FIG. 4 is a perspective view of a part of a middle plate of the first preferred embodiment of the present disclosure.

Referring to FIGS. 2, 4 and 6, the middle plate 30 may be made of an insulated material with acceptable thermal conductivity, such as glass fiber-reinforced resin and is disposed between the upper plate 10 and the lower plate 20. The middle plate 30 includes an upper surface 31, a lower surface 32, four middle heating holes 33, four middle receiving holes 34 each located adjacent to one of the four middle heating holes 33, four middle conductive layers 35, a straight middle through groove 37 corresponding in location to the upper longitudinal through groove 19 and the lower longitudinal through groove 29, two L-shaped middle through grooves 37', and one middle partition 301 defined by the straight middle through groove 37 and two L-shaped middle through grooves 37'. The middle heating holes 33 and the middle receiving holes 34 are located at the middle partition 301. The middle conductive layer 35 may be made of a material having good electrical conductivity and thermal conductivity properties, such as copper or the like. The middle conductive layer 35 has an upper region 351 formed on the upper surface 31 and surrounding the middle heating hole 33, a lower region 352 formed on the lower surface 32 and surrounding the middle heating hole 33, and a heating tube region 353 formed on a wall of the middle heating hole 33 and connected to the upper region 351 and the lower region 352. The upper region 351 and the lower region 352 are respectively shaped as, but not limited to, a ring. In alternate embodiment, the number of the middle receiving hole 34 located adjacent to each middle heating hole 33 is not particularly limited, i.e., one or more middle receiving holes 34 may be formed adjacent to each middle heating hole 33, and the shape of the middle through grooves 37, 37' can be changed according to the actual need. When the upper plate 10, the middle plate 30 and the lower plate 20 are stacked together in order, the upper heating hole 13, the middle heating hole 33 and the lower heating hole 23 are connected together to form a heating through hole 50, and the upper receiving hole 14, the middle receiving hole 34 and the lower receiving hole 24 are connected together to form a receiving through hole 60. As such, the lower region 352 of the middle conductive layer 35 is connected to the upper region 261 of the second lower conductive layer 26 to enable heat and electricity transfer therebetween; however, the lower region 352 is not connected to the upper region 251 of the first lower conductive layer 25. In addition, the upper region 351 of the middle conductive layer 35 is connected to the lower region 152 of the upper conductive layer 15 to enable heat and electricity transfer therebetween. In alternate embodiments, the surfaces of the upper conductive layer 15, the middle conductive layer 35, and the second lower conductive layer 26 may be covered individually with a solder mask, so that heat can be transferred between each conductive layer whereas electricity cannot be transferred therebetween.

Each electric heating element 40 is arranged in one of the four receiving through holes 60 and has two terminals. One of the terminals is connected electrically to the upper conductive layer 15 and the other one is connected electrically to the first lower conductive layer 25. In this embodiment, the electric heating element 40 is an electrical resistance heater and two terminals thereof are respectively connected electrically to the upper conductive layer 15 and the first lower conductive layer 25 by tin soldering. In another embodiment, the type of the electric heating element 40 can be changed according to the actual need.

Figure 7:
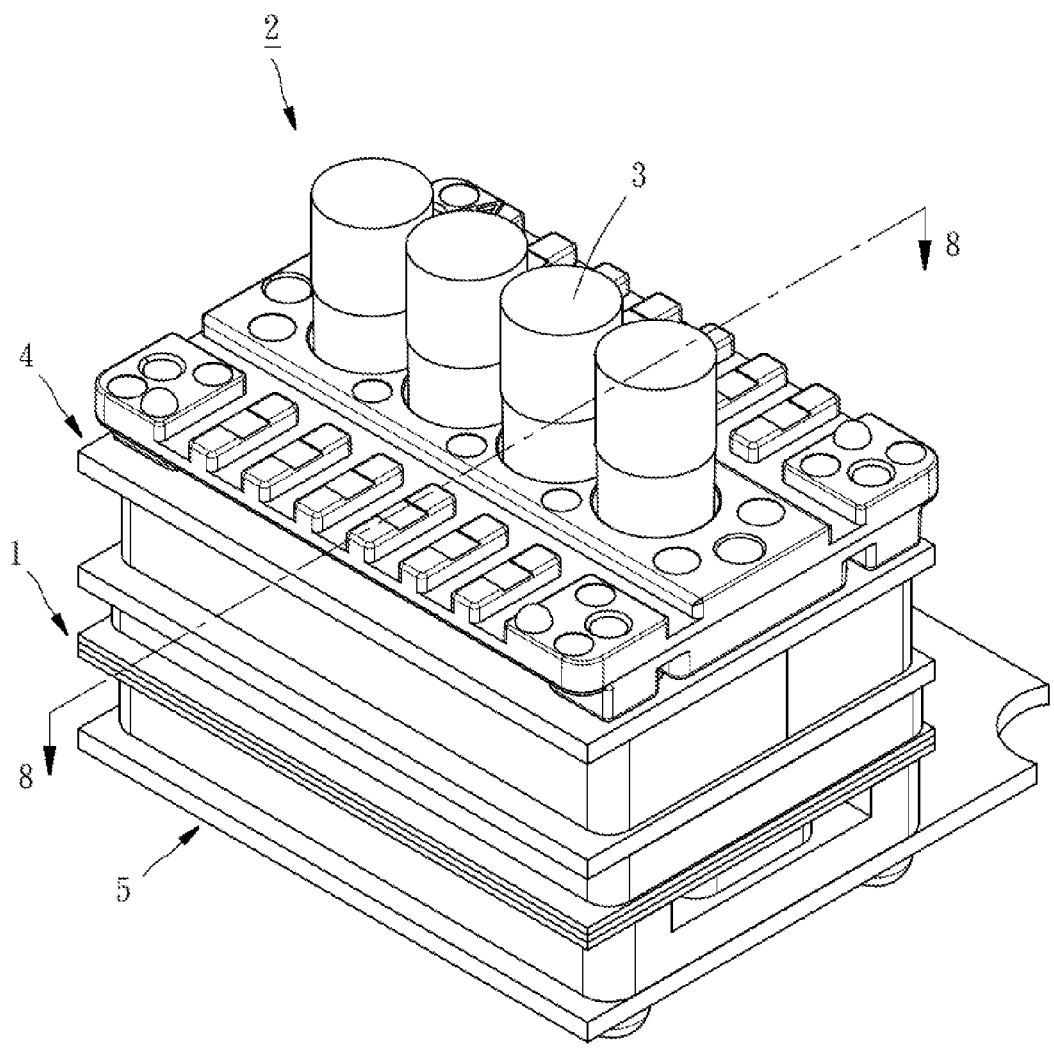
FIG. 7 is a perspective view of a biochemical reactor of the first preferred embodiment of the present disclosure.
Figure 8:
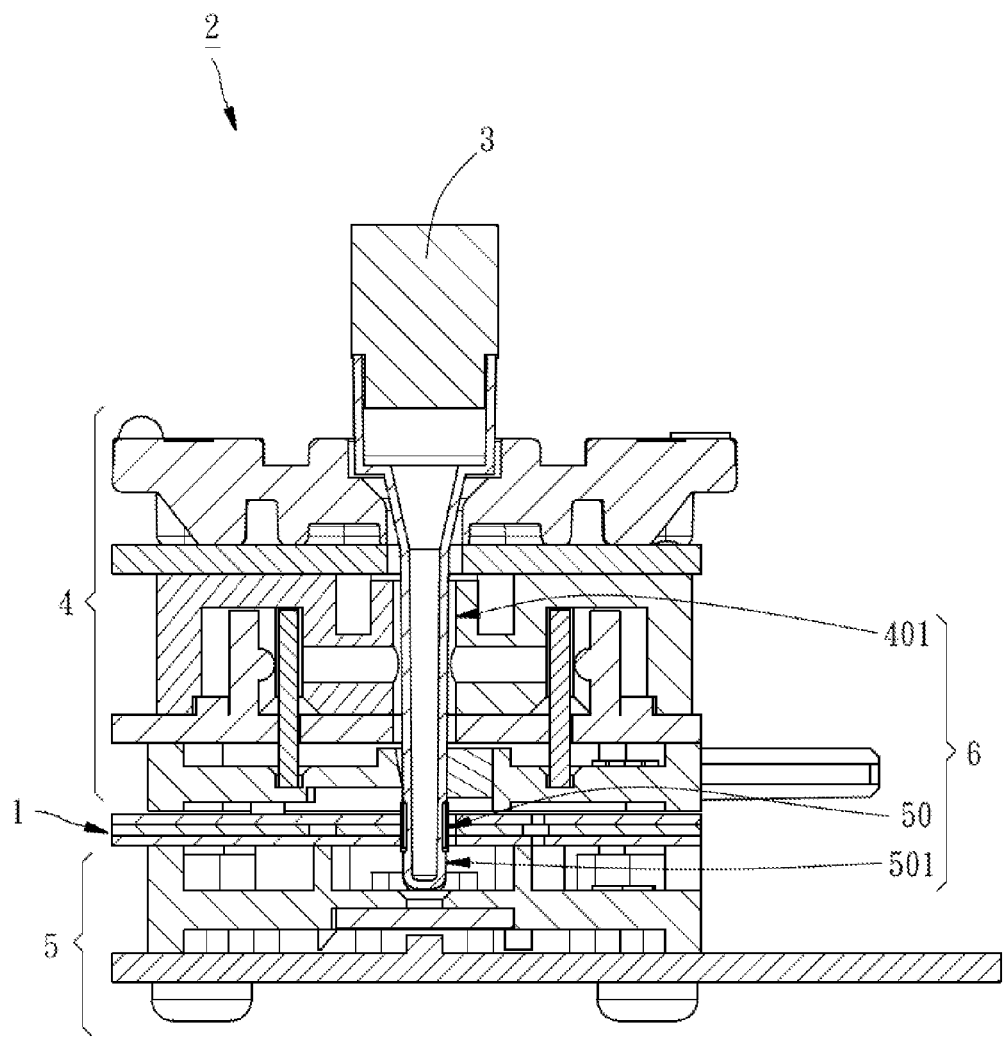
FIG. 8 is a cross-sectional view taken along line 8-8 of FIG. 7.

The present disclosure further provides a biochemical reactor 2 having the heating device 1 for the insertion of four vessels 3. As shown in FIGS. 7 and 8, the biochemical reactor 2 comprises a first body 4 having four first holes 401, and a second body 5 located under the first body 4 and having four second holes 501, the heating device 1 disposed between the first body 4 and the second body 5. Each heating through hole 50 and the corresponding first and second holes 401, 501 are connected together to form a vessel receiving groove 6. In this embodiment. The biochemical reactor 2 includes four vessel receiving grooves 6 adapted for the insertion of the four vessels 3, respectively. In alternate embodiments, the number of the vessel receiving groove 6 can be varied according to the actual need.

By means of the above-disclosed construction and features, the heating device 1 can provide heat energy to the heating through hole 50 by the electric heating element 40 to maintain the temperature of a part of the vessel 3 at a steady temperature, such that a biochemical reaction can be carried out in the vessel 3. In practical application, a power supply (now shown) is used to provide electricity to the electric heating element 40 through the upper conductive layer 15 and the first lower conductive layer 25. After the electric heating element 40 is powered, the electric heating element 40 converts the electricity energy into heat energy, which is then transferred to the heating through hole 50 through the tin soldering, the upper conductive layer 15, the air in the receiving through hole 60, the middle conductive layer 35, the first lower conductive layer 25, the second lower conductive layer 26, and the upper, middle and lower plates 10, 30, 20. Because the lower region 152 of the upper conductive layer 15 surrounding the upper receiving hole 14 plays a role for supplementarily facilitating heat conduction of the upper plate 10, it can be omitted in alternate embodiments depending on the circumstances. The upper region 251 of the first lower conductive layer 25 plays a role for supplementarily facilitating heat conduction of the lower plate 20. In alternate embodiments, the upper region 251 may be configured only to surround the lower receiving hole 24 without surrounding the lower heating hole 23, and even can be omitted. By means of the present disclosure, the heating through hole 50 can reach a homogeneous heating temperature to maintain the temperature of a part of the vessel 3 at a steady temperature, so that a biochemical reaction can be carried out in the vessel 3. In fact, some parts of the conductive layers can be omitted except for the upper region 151 and the receiving tube region 153 of the upper conductive layer 15 and the receiving tube region 253 and the lower region 252 of the first lower conductive layer 25. However, the heat conducting effect of a heating device without some parts of the conductive layers may be reduced slightly.

Because the upper plate 10 has a plurality of upper elongated through grooves 17, the upper partitions 101 may have elasticity to adsorb the stress caused by expansion and contraction of the electric heating element 40. Accordingly, the probability of crack at the soldering joints of the electric heating element 40 and the upper conductive layer 15 can be reduced effectively so that the lifetime of the heating device 1 can be increased. The upper longitudinal through groove 19 may further increase the elastic deformation of the upper partition 101. In a condition that the upper plate 10 has elasticity to absorb the stress caused by expansion and contraction of the electric heating element 40, the upper elongated through grooves 17 and the upper longitudinal through groove 19 can be omitted. On the other hand, because the hole groups 18 are separated by the upper elongated through grooves 17, the heat energy of each electric heating element 40 located at one of the upper partitions 101 may not be dissipated to other upper partitions 101, such that each upper heating hole 13 may have a uniform and steady heating efficiency. However, the upper elongated through grooves 17 can also be omitted. Similarly, the lower elongated through grooves 27 and the lower longitudinal through groove 29 of the lower plate 20 and the lower partitions 201 may also have the above-mentioned properties, and therefore it will not be repeated here.

The construction that the middle through grooves 37, 37' surrounding the middle heating holes 33 and the middle receiving holes 34 can substantially retain the heat energy generated by each electric heating element 40 in middle partition 301, such that each middle heating hole 33 may obtain a uniform heating temperature. However, the middle through grooves 37, 37' can also be omitted.

Because the upper plate 10, the middle plate 30, and the lower plate 20 of the heating device 1 can be made by a known process of printed circuit board, the configuration of the heating device 1 is lightweight and the manufacturing process is time-saving. The upper plate 10, the middle plate 30 and the lower plate 20 can be stacked sequentially and fixed to each other by a plurality of bolts of adhered to each other by adhesive layers such as double-sided adhesive films, tapes or the like. In alternate embodiment, the combination of the upper plate 10, middle plate 30 and lower plate 20 (hereinafter referred to as "assembled plate") can be disposed in the biochemical reactor 2 in an upside-down manner. The receiving through hole 60 is not a closed space because of the gaps between the plates, so that a vacuum suction resulted from volume reduction of air in the receiving through hole 60 due to temperature decrease will not be generated in the process of soldering the electric heating element 40 to the upper and the lower plates 10, 20 during cooling of the tin soldering. As a result, the molten tin soldering will not be sucked into the space between the electric heating element 40 and the wall of the receiving through hole 60, thereby avoiding short-circuit caused by connection of the molten tin solderings from two terminals of the electric heating element 40. Even though the molten tin soldering may penetrate into the space between the electric heating element 40 and the wall of the receiving through hole 60 by capillary action or force of gravity; the molten tin soldering can only penetrate into the upper receiving hole 14 covered with the upper conductive layer 15 and the lower receiving hole 24 covered with the first lower conductive layer 25, and cannot penetrate into the middle receiving hole 34 without being covered with conductive layer because tin soldering may only attach on conductive layer and the wall of the middle receiving hole 34 is not coated with conductive layer thereon. Therefore, the short-circuit caused by connection of the molten tin solderings from two terminals of the electric heating element 40 can be further avoided and thus the production yield can be improved effectively.

Figure 9:
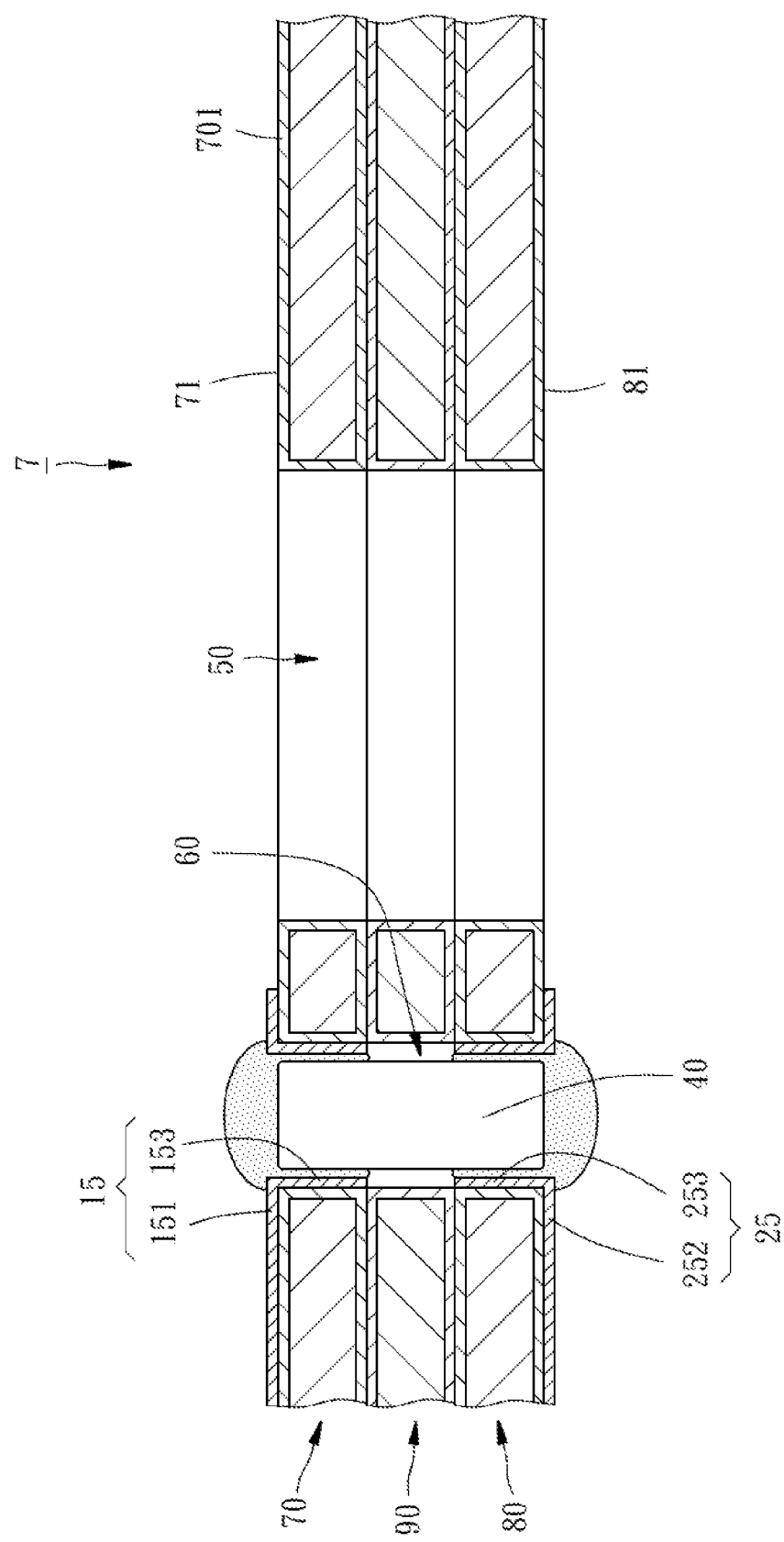
FIG. 9 is a cross-sectional view of a heating device of a second preferred embodiment of the present disclosure.

The material of the upper plate 10, the middle plate 30 and the lower plate 20 may be varied. For example, another heating device 7 according to a second embodiment is shown in FIG. 9. An upper plate 70, a middle plate 90 and a lower plate SO are respectively made of a conductive material covered with an insulated layer 701. The conductive material may be aluminum or iron such that it has a high thermal conductivity. In comparison with the first embodiment, because the heat conducting capacities of the upper, middle and lower plates 70, 90, 80 are better than those of the upper, middle and lower plates 10, 30, 20, some parts of the conductive layers can be selectively omitted to simplify the manufacturing process. As an example, in this embodiment, the heating tube region 154, or the part of the upper region 151 or the lower region 152 of the upper conductive layer 15 surrounding the upper heating hole 13 may be omitted; the heating tube region 263, or the upper region 261 or the lower region 262 of the second lower conductive layer 26 may be omitted; parts of the lower region 252 and the upper region 251 of the first lower conductive layer 25 surrounding the second lower conductive layer 26 may be omitted; and the heating tube region 353, the upper region 351, or the lower region 352 of the middle conductive layer 35 may be omitted. Although some parts of the conductive layers are omitted, the heat energy produced from the electric heating element 40 can still be transferred effectively to the heating through hole 50. In the present embodiment, the heating device 7 still comprises some conductive layers for electrically connecting the electric heating element 40 through tin soldering, thus the upper conductive layer 15 disposed on the upper plate 70 has the upper region 151 and the receiving tube region 153, and the first lower conductive layer 25 disposed on the lower plate 80 has the lower region 252 and the receiving tube region 253.

It should be understood that the detailed descriptions mentioned above, while indicating preferred embodiments of the invention, are given by way of illustration only, and thus are not limitative of the present disclosure. Such variations are not to be regarded as a departure from the spirit and scope of the invention, and all such modifications as would be obvious to one skilled in the art are intended to be included within the scope of the following claims.

What is claimed is:

1. A heating device comprising:
   an upper plate including an upper heating hole, at least one upper receiving hole located adjacent to the upper heating hole, and an upper conductive layer having an upper region formed on an upper surface of the upper plate and surrounding the upper receiving hole, and a receiving tube region formed on a wall of the upper receiving hole and connected to the upper region of the upper conductive layer;
   a lower plate including a lower heating hole, at least one lower receiving hole located adjacent to the lower heating hole, and a first lower conductive layer having a lower region formed on a lower surface of the lower plate and surrounding the lower receiving hole, and a receiving tube region formed on a wall of the lower receiving hole and connected to the lower region of the first lower conductive layer;
   a middle plate disposed between the upper plate and the lower plate and including a middle heating hole and at least one middle receiving hole located adjacent to the middle heating hole; wherein the upper heating hole, the middle heating hole and the lower heating hole are connected together to form a heating through hole, and the upper receiving hole, the middle receiving hole and the lower receiving hole are connected together to form a receiving through hole; and
   an electric heating element disposed in the receiving through hole and having two terminals connected electrically to the upper conductive layer and the first lower conductive layer, respectively.

2. The heating device as claimed in claim 1, wherein the upper region of the upper conductive layer further surrounds the upper heating hole; the upper conductive layer further has a lower region formed on a lower surface of the upper plate and surrounding the upper heating hole, and a heating tube region formed on a wall of the upper heating hole and connected to the upper region and the lower region of the upper conductive layer; the lower plate further includes a second lower conductive layer having a lower region formed on the lower surface of the lower plate and surrounding the lower heating hole, an upper region formed on an upper surface of the lower plate and surrounding the lower heating hole, and a heating tube region formed on a wall of the lower heating hole and connected to the upper region and the lower region of the second lower conductive layer; the lower region of the first lower conductive layer further surrounds the lower region of the second lower conductive layer and is spaced from the lower region of the second lower conductive layer at a predetermined distance; the middle plate further includes a middle conductive layer having an upper region formed on an upper surface of the middle plate and surrounding the middle heating hole, a lower region formed on a lower surface of the middle plate and surrounding the middle heating hole, and a heating tube region formed on a wall of the middle heating hole and connected to the upper region and the lower region of the middle conductive layer.

3. The heating device as claimed in claim 2, wherein the lower region of the upper conductive layer further surrounds the upper receiving hole and is connected to the receiving tube region of the upper conductive layer.

4. The heating device as claimed in claim 2, wherein the first lower conductive layer further has an upper region formed on the upper surface of the lower plate, surrounding the lower receiving hole and the upper region of the second lower conductive layer, and connected to the receiving tube region of the first lower conductive layer; the upper region of the first lower conductive layer is space from the upper region of the second lower conductive layer at a predetermined distance.

5. The heating device as claimed in claim 1, wherein the upper plate includes a plurality of the upper heating holes and a plurality of upper elongated through grooves; at least one of the upper receiving holes is located adjacent to each said upper heating hole; each said upper heating hole and the upper receiving hole located adjacent thereto form a hole group; each said hole group is located between two said upper elongated through grooves.

6. The heating device as claimed in claim 1, wherein the lower plate includes a plurality of the lower heating holes and a plurality of lower elongated through grooves; at least one of the lower receiving holes is located adjacent to each said lower heating hole; each said lower heating hole and the lower receiving hole located adjacent thereto form a hole group; each said hole group is located between two said lower elongated through grooves.

7. The heating device as claimed in claim 1, wherein the middle plate includes a plurality of middle heating holes and a plurality of middle through grooves; at least one of the middle receiving holes is located adjacent to each said middle heating hole; the plurality of middle through grooves surround the middle heating holes and the middle receiving holes.

8. The heating device as claimed in claim 1, wherein the upper plate, the middle plate and the lower plate are respectively made of an insulated material or a conductive material covered with an insulated layer.

9. A biochemical reactor adapted for insertion of a vessel, the biochemical reactor comprising:
- a first body having a first through hole;
- a second body located under the first body and having a second through hole; and
- a heating device as claimed in claim 1, the heating device being disposed between the first body and the second body;
- wherein the heating through hole, the first through hole and the second through hole are connected together to form a vessel receiving groove for the insertion of the vessel.

\* \* \* \* \*